United States Patent [19]
Lichowsky et al.

[11] 3,935,984
[45] Feb. 3, 1976

[54] AUTOMATIC CUFF MECHANISM FOR BLOOD PRESSURE MEASURING SYSTEM

[75] Inventors: Abraham Lichowsky, Los Angeles; Jack I. Bauman, Santa Monica, both of Calif.

[73] Assignees: Ambitex Company; Medical Monitors, Inc., both of Los Angeles, Calif.; part interest to each

[22] Filed: Sept. 9, 1974

[21] Appl. No.: 504,131

[52] U.S. Cl. .................... 128/2.05 C; 128/2.05 M
[51] Int. Cl.² ............................................. A61B 5/02
[58] Field of Search ..... 128/2.05 C, 2.05 A, 2.05 G, 128/2.05 M, 2.05 S, 327

[56] References Cited
UNITED STATES PATENTS

| | | | |
|---|---|---|---|
| 2,020,469 | 11/1935 | Laufman et al. | 128/2.05 G |
| 2,053,383 | 9/1936 | Telson et al. | 128/2.05 M |
| 2,149,690 | 3/1939 | Snyder | 128/2.05 M |
| 2,714,379 | 8/1955 | Raines | 128/2.05 G |
| 3,095,873 | 7/1963 | Edmunds, Jr. | 128/2.05 A |
| 3,621,831 | 11/1971 | Pisacano | 128/2.05 C |
| 3,757,772 | 9/1973 | Goldblat et al. | 128/2.05 C |

FOREIGN PATENTS OR APPLICATIONS

| | | | |
|---|---|---|---|
| 926,646 | 12/1949 | France | 128/2.05 G |
| 805,599 | 8/1936 | France | 128/2.05 G |

Primary Examiner—Kyle L. Howell
Attorney, Agent, or Firm—Ralph B. Pastoriza

[57] ABSTRACT

An automatic cuff for use with blood pressure measuring apparatus includes a cylindrical member within which a person may position his arm. A flexible band is positioned circumferentially about the inner wall of the cylinder and connected to a cable extending from the cylinder such that pulling on the cable circumferentially contracts the band in the manner of a tightening spiral. The band supports an air chamber on its inner wall and after a person's arm is snugly engaged by the band, further contraction is stopped and fluid is pumped in the fluid chamber to provide additional force in closing off circulation. After the air pressure is gradually decreased, release of the person's arm is accomplished by releasing the pulling force on the cable so that the flexible band circumferentially expands under its own natural bias.

5 Claims, 4 Drawing Figures

AUTOMATIC CUFF MECHANISM FOR BLOOD PRESSURE MEASURING SYSTEM

This invention relates to automatic blood pressure measuring apparatus and more particularly to the cuff portion of such apparatus for temporarily closing off blood circulation in a portion of a person's body, for example, an arm or leg, in accord with sequencing steps in automatically taking a person's blood pressure.

BACKGROUND OF THE INVENTION

In copending patent applicaton Ser. No. 443,442 filed Feb. 19, 1974 and entitled "BLOOD PRESSURE MEASURING SYSTEM" there is disclosed a system for automatically taking a person's blood pressure. One of the steps involved in the process includes wrapping the person's arm in a cuff which includes a fluid chamber for temporarily cutting off blood flow circulation. While a conventional type cuff could be used with the apparatus described in the aforementioned application provided suitable fluid line connections were made to the apparatus as well as provision for a suitable acoustic pulse pick-up means, it would be desirable to provide a completely automatic arrangement for providing the necessary blood circulation cut off.

With such an automatic cuff applicator, consistent snug engagement of the person's arm could be realized all to the end that more consistent results can be realized. A desirable feature of any type of automatic cuff applicator would be the provision of suitable acoustic pulse detecting means for connection into the overall blood pressure measuring system.

A further desirable feature in such an automatic cuff applicator is to provide suitable support means to assure that a patient's arm or other portion of his body to which the cuff is applied remains relatively stationary during the blood pressure measuring operation. By providing for a stationary comfortable positioning of the arm or other portion, the risk of generation of undesirable artifacts resulting in erroneous signals in the system is minimized.

BRIEF DESCRIPTION OF THE PRESENT INVENTION

With the foregoing in mind, the present invention contemplates an automatic cuff mechanism for use with an automatic blood pressure taking apparatus such as shown and described in the heretofore mentioned copending application, incorporating the aforementioned desirable features.

More particularly, in accord with the invention, the cuff mechanism includes a cylindrical member defining an opening for receiving a portion of a person's body such as his arm in which blood circulation is to be temporarily cut off. Mechanical contracting means are provided in the opening adapted upon operation to close about the patient's arm. The mechanical contracting apparatus is designed to incorporate means responsive to a given resistance force exerted by the patient's arm resisting further contraction of the contracting means to automatically terminate operation thereof so that the contracting means engages about the person's arm in a snug but comfortable manner. A flexible fluid chamber is supported by the contracting means in a position such that further pressure can be exerted on the patient's arm by filling the fluid chamber with fluid.

An important feature of this invention is the provision of an integrally built-in acoustic cavity formed in the exterior wall of the flexible fluid chamber. The arrangement and positioning is such that the acoustic cavity can seal about the portion of the person's arm so that with a passage extending from the completely closed acoustic cavity suitable acoustic pulses can be readily detected by a microphone exterior of the cylindrical member.

The mechanical contracting means as well as the flow of fluid into and out of the chamber are all sequentially controlled by the main blood pressure taking apparatus.

BRIEF DESCRIPTION OF THE DRAWINGS

A better understanding of this invention will be had by referring to a preferred embodiment thereof as illustrated in the accompanying drawings in which.

DETAILED DESCRIPTION OF THE PREFERRED EMBODIMENT

Figure 1:
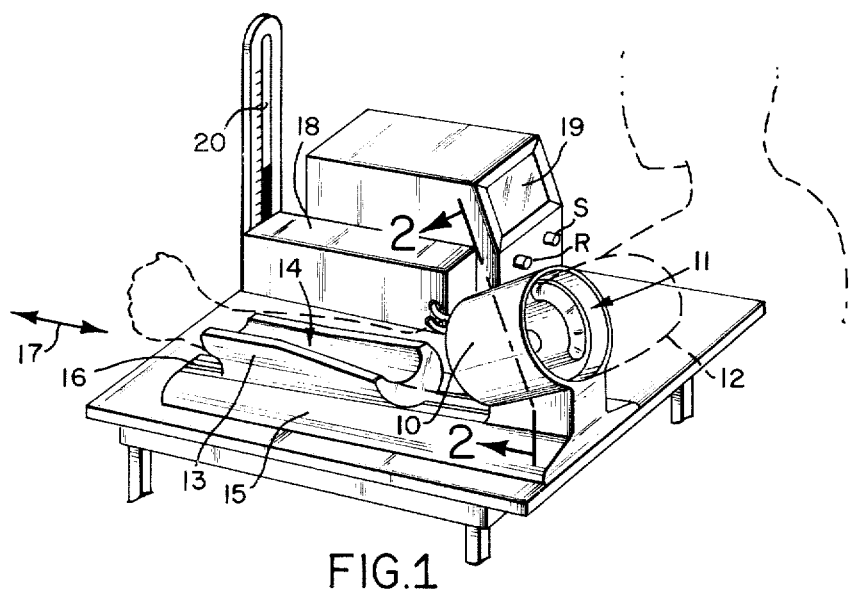
FIG. 1 is a perspective view of the cuff mechanism in conjunction with other components for automatically taking a person's blood pressure.

Referring first to FIG. 1, the cuff mechanism for the blood pressure measuring system includes a cylindrical member 10 defining an opening 11 for receiving a portion of a person's body in which blood circulation is to be temporarily cut off. In the particular embodiment illustrated, a person's arm is illustrated in dotted lines at 12 positioned within the opening preparatory to having a blood pressure measurement made.

It is desirable that the person's arm in the system described remain stationary during the measuring process and towards this end, there is provided a forearm rest 13 defining a cradle 14 slidably mounted on a base plate 15. The cylindrical member 10 may conveniently be mounted on the forward portion of the base plate 15 and by providing a slidable arrangement such as tracks 16 for the forearm rest, it may be longitudinally adjusted relative to the exit end of the opening 11 all as indicated by the double-headed arrow 17.

In addition to the cuff mechanism generally described thus far, there is provided a controller 18 and a display means 19. If desired, there may also be included a mercury manometer 20 positioned on the controller 18 for convenient viewing by a patient during the blood pressure measuring operation. However, it will be understood that the actual systolic and diastolic blood pressures will be indicated on the display 19 when the measuring has been completed and no manometer is necessary.

As shown in FIG. 1, the display means 19 may include a start push-button S or coin-operated starter, and a reset push-button R. The arrangement is such that after a patient has positioned his arm within the opening, by depressing the start button S, the various steps involved in making a blood pressure measurement are carried out completely automatically. When the measurement has been completed, the arm is automatically released from the cuff mechanism and operation of the reset button will remove the display on the screen of the final blood pressure and place the sytem in condition preparatory to making a subsequent blood pressure measurement.

As mentioned heretofore, the present invention is concerned with the cuff mechanism itself for use with the blood pressure measuring apparatus and thus a detailed description of the operation of making an actual blood pressure measurement need not be set forth. Reference is had to the heretofore mentioned copending application with respect to the sequential operation of making such blood pressure measurements and displaying the same.

Figure 2:
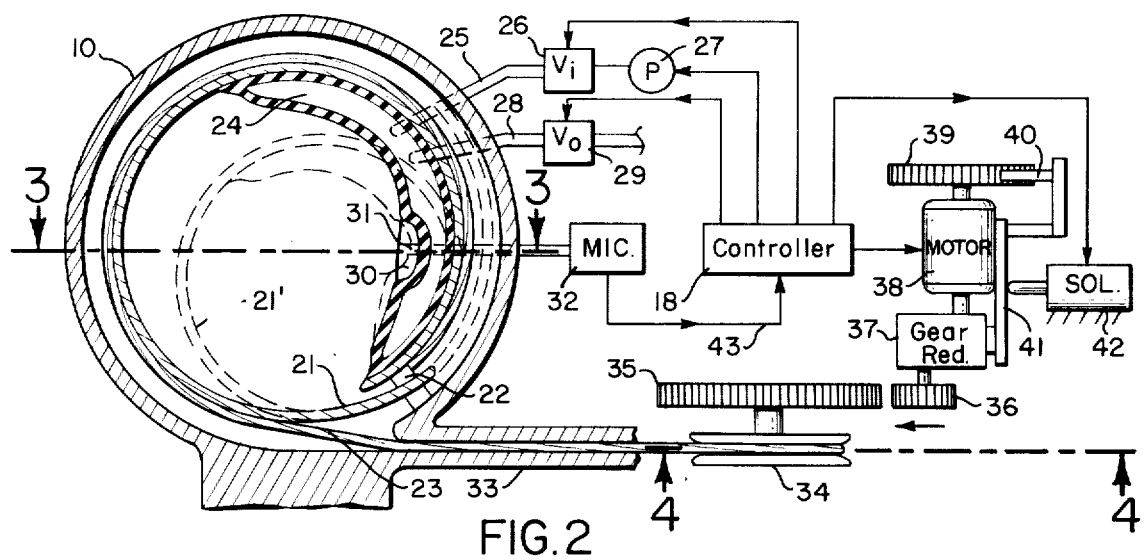
FIG. 2 is an enlarged fragmentary cross section of the cuff mechanism taken in the direction of the arrows 2—2 of FIG. 1 wherein certain operating components are shown schematically.

Referring now to FIG. 2, further details of the cuff mechanism will be evident. As shown, a mechanical contracting means is provided within the cylindrical member 10 in the form of a flexible band 21 having one end secured at its outer corners to the inner wall of the cylindrical opening as indicated at 22. The band extends circumferentially about the interior of the opening in a spiral-like manner. A cable 23 connects to the band and in the particular embodiment disclosed preferably wraps about the exterior central portion of the band, the inner end of the cable being anchored at the same anchor point 22 for the inner end of the band.

As shown in FIG. 2, the cable 23 passes from the flexible band 21 tangentially out the cylindrical member 10. With this arrangement, it will be evident that if a pulling force is applied to the cable 23, it will circumferentially contract the band in the manner of a tightening spiral. This action is illustrated by the dotted line position 21' of the band after the cable 23 has been pulled wherein it will be noted that the outer end of the band has passed between the securing portions 22 to pass about the inside periphery of the cylindrical member 10 all as shown by the dotted lines.

It should be understood that the tightening of the flexible band as described results in an action similar to wrapping a bandage about a person's arm. In other words, there is no relative motion between the band and the person's arm in a circumferential direction but rather only a successive radial engagement of the arm as the band is effectively wrapped about the arm. The process is substantially the same, as mentioned, as takes place when a bandage is wrapped about a person's arm or a conventional blood measuring cuff is wrapped about a person's arm.

Cooperating with the flexible band 21 is a fluid chamber 24 lying along a portion of the interior surface of the band. Fluid for filling the chamber is passed into the chamber through an inlet tube or line 25 under control of an inlet valve 26 the other side of which connects to a fluid pump 27. Releasing of fluid pressure from the fluid chamber 24 takes place through an outlet line or passage 28 through an outlet valve 29.

An important feature of this invention resides in the provision of an acoustic cavity formed in the exterior wall of the fluid chamber 24 as indicated at 30. This cavity is positioned to engage preferably over an artery of the person's arm within the opening of the cylindrical member in a sealing relationship when fluid has been pumped into the chamber. The acoustic cavity 30 is in communication through passage 31 with an exteriorally located microphone 32.

Referring now to the lower portion of FIG. 2, the outer end of the cable 23 passes through an extension housing 33 integrally formed with the cylindrical member 10 as shown. This cable wraps about a drum 34 carrying on its shaft a gear 35. A drive gear 36 is arranged to be placed in engagement with a gear 35 to drive the drum 34 when it is desired to contract the flexible band. As shown, gear 36 is connected to the output of a gear reduction train 37 in turn connected to a motor 38. Ratchet means in the form of a ratchet gear 39 connected directly to the motor shaft and a cooperating pawl 40 prevent counter-rotation of the motor and thus counter-rotation of the gear 35 and drum 34 when the driving gear 36 is in meshing engagement with the gear 35.

As shown in FIG. 2, the driving gear 36, gear reduction train 37, motor 38, and ratchet wheel and pawl mechanism 39 and 40 are all supported on a flexible flexure type mounting 41. A solenoid 42 is arranged to urge these components to the left as viewed in FIG. 2 when energized thereby causing engagement of the drive gear 36 with the gear 35.

The controller 18 described in FIG. 1 is shown in block form in FIG. 2 and includes outlet control lines connecting to the solenoid 42, motor 38, inlet valve 26, pump 27 and outlet valve 29. This controller also includes the various electrical components utilized in effecting a blood pressure measurement and towards this end is arranged to receive on line 43 electrical pulse signals from the microphone 32, generated in response to the acoustic pulses from the acoustic cavity 30.

Figures 3, 4:
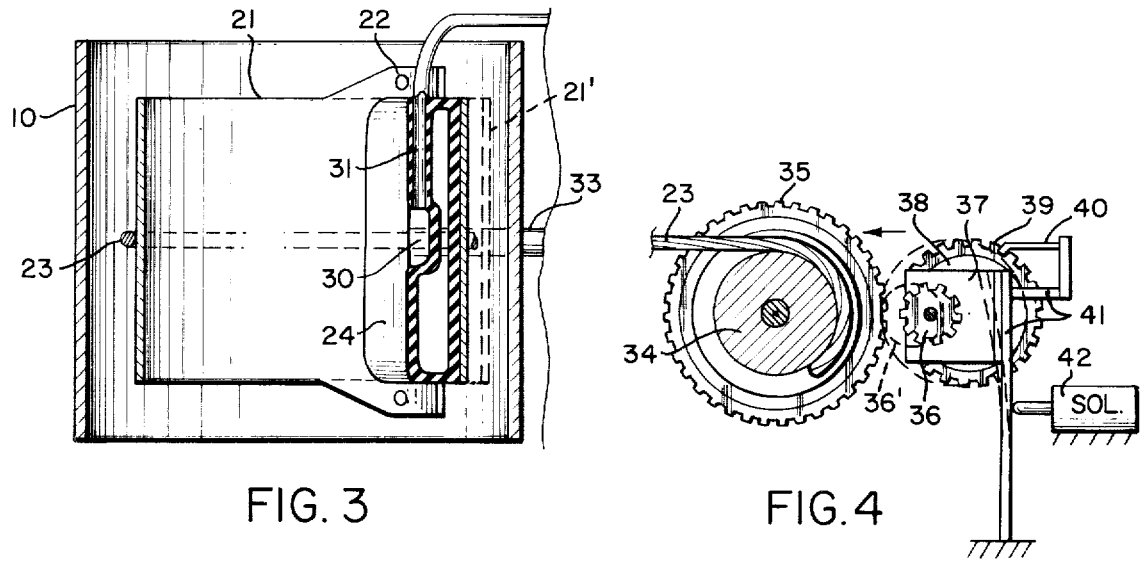
FIG. 3 is another fragmentary cross section of the cuff mechanism taken in the direction of the arrows 3—3 of FIG. 2; and, FIG. 4 is a front cross section looking in the direction of the arrows 4—4 of FIG. 2.

In the cross section of FIG. 3, the manner in which the inner end of the flexible band 21 is anchored to the cylindrical member 10 as at 22 will be clear. Thus, this inner end of the band includes a widened portion so that it will not interfere with the outer or free end of the band indicated in dotted lines at 21' from sliding upwardly as viewed in FIG. 3 when the spiral configuration is contracted.

Also in FIG. 3, the passage 31 from the acoustic cavity 30 is shown as integrally built into the exterior wall of the fluid member 24.

Finally, the central positioning of the cable 23 will be clear from the FIG. 3 showing, the outer end of the cable passing through the housing 33 to connect to the drum 34 as described in FIG. 2.

The foregoing will become clearer by referring to the front cross section of FIG. 4 wherein the cable 23 is shown wrapped partially around and secured to the drum 34. When the drive gear 36 is separated or out-of-engagement with the gear 35, the gear reduction train 37, motor 38, ratchet gear 39 and pawl 40 are all in the solid lined positions shown. When the solenoid 42 is energized, it will urge the flexible mounting 41 to the left as viewed in FIG. 4 so that the drive gear 36 and other components carried by the mounting 41 assume the dotted line positions such as illustrated at 36' wherein engagement takes place with the gear 35 to thereby drive the drum 34.

The motor 38 described in FIGS. 2 and 4 is designed to exert a given torque. Any resistance force to rotation of the motor above a given value will thus result in the motor simply stopping since it is incapable of exceeding the designed-in torque.

OPERATION

With the foregoing description in mind, the operation of the cuff mechanism of this invention will be evident. Thus, with reference to FIG. 1 a patient or other person who wishes to have his blood pressure measured will initially insert his left arm into the opening 11 so that his forearm will rest in the cradle 14. Thereafter, he can simply depress the start button S in FIG. 1.

Referring to FIG. 2, operation of the start button initiates various sequences involved in taking the blood pressure. Initially, the solenoid 42 will be operated simultaneously with starting of the motor 38 so that immediately the gear 35 will be driven by the gear 36 in a direction to pull the cable 23 to the right as viewed in FIG. 2. The gear reduction 37 slows down considerably the rotary motion of the drum 34 relative to the speed of the motor 38 but nevertheless the circumferential contraction of the flexible band takes place relatively quickly until the fluid chamber and band are snugly wrapped about the patient's arm. The resistance exerted by the patient's arm to further contraction will automatically stop the motor 38 since, as mentioned, it is designed to only exert a given torque. The given torque is such as to assure that the flexible band snugly engages a person's arm but in a comfortable manner.

It will also be noted that as a consequence of the ratchet wheel 39 and pawl 40, counter-rotation of the motor and thus the various gears and drum is prevented so that the contracted band will remain in its final snug position about the patient's arm.

After the mechanical contraction of the band has been completed as described, fluid will then be pumped into the fluid chamber 24 by opening the inlet valve 26 which is under control of the controller 18. As the fluid pressure increases in successive steps, detection of acoustic pulses by the microphone 32 controls the controller in such a manner as to close off further fluid to the fluid chamber after assurance is had that the blood circulation is completely cut off.

After circulation has been cut off, the fluid in the chamber is then released very gradually by the outlet control valve 29 also under control of the controller 18 until such time as proper pulses are detected by the microphone as a consequence of the resumption of blood flow.

The manometer 20 shown in FIG. 1 may be connected directly to the fluid chamber 24 if desired simply to provide the patient with a visual indication of what is happening during the operation of the system. The actual determination of the direct systolic and diastolic blood pressures, however takes place in the controller and when the blood circulation has started to flow as a consequence of decreased fluid pressure in the fluid chamber, the computed blood pressure values will be displayed on the screen 19 of FIG. 1. Thereafter, the solenoid 42 will be automatically de-energized thereby releasing the drive gear 36 from the gear 35 and immediately permitting the flexible band 21 in the cylindrical member 10 to circumferentially expand under its inherent bias. The patient's arm is thus released. The displayed blood pressures will remain on the display screen 19 until the reset button R in FIG. 1 is depressed. This action removes the displayed values and prepares the equipment for making a subsequent measurement.

Because of the flexure mounting of the motor drive arrangement for the drum 34 and the requirement that the solenoid 42 be energized in order to cause engagement of the drive gear, the system is fail-safe in that should there occur a power failure, the solenoid is de-energized and disengagement takes place immediately permitting the band to open up completely and release the patient's arm.

Further, the feature of designing the electric motor 38 to exert only a given torque assures that regardless of a person's arm size, the same snug engaging pressure will always be applied.

While a cylinder has been shown for receiving the person's arm, a clam shell or equivalent enclosing member could be used.

From the foregoing description, it will be evident that an automatic cuff mechanism for use with automatic blood pressure measuring equipment has been provided.

What is claimed is:

1. An automatic cuff mechanism for use with a blood pressure measuring system, comprising, in combination:
   a. an enclosing member defining an opening for receiving a portion of a person's body in which blood circulation is to be temporarily cut off;
   b. mechanical contracting means including a flexible band having one end secured to an inner wall portion of said opening in said enclosing member, said band passing circumferentially about the interior of said opening; and pulling means secured to said band and passing tangentially therefrom out said enclosing member such that a pulling force on said pulling means circumferentially contracts said band in a manner of a tightening spiral to close about said portion;
   c. means responsive to a given resistance force exerted by said portion resisting further contraction of said contracting means to terminate operation thereof so that said contracting means engages about said portion in a snug manner; and
   d. a flexible fluid chamber lying along a portion of the interior surface of said band, in a position between said flexible band and said portion of a person's body such that further pressure can be exerted on said portion by filling said flexible fluid chamber with fluid.

2. The subject matter of claim 1 in which said means responsive to a given resistance force includes a motor having a drum connected to said pulling means and capable of exerting up to a given maximum torque on said drum as determined by said resistance force, whereby when said resistance force is reached, said motor stops; and ratchet means for preventing counter-rotation of said motor.

3. The subject matter of claim 2, additionally including holding means for holding said motor in engagement with said drum so that upon deactuation of said holding means said motor disengages said drum and said band is free to circumferentially expand from its own inherent bias to thereby release its engagement with said portion of said person's body.

4. The subject matter of claim 1, in which an exterior wall portion of said flexible fluid chamber is shaped to define an acoustic cavity juxtaposed to said portion of a person's body so that said cavity is sealed against said portion when said chamber is inflated with fluid; and a passage means in the wall of the cavity extending from said acoustic cavity for connection to a microphone.

5. The subject matter of claim 1, in which said enclosing member comprises a cylindrical member; and a base plate mounting said cylindrical member at its forward portion; and a forearm rest adjacent to the exit end of said opening and slidably coupled to said base plate so that it may be adjusted to properly support the forearm of a person in proper relationship to the automatic cuff and acoustic cavity when said portion of said person's body is his arm.

* * * * *

UNITED STATES PATENT OFFICE
CERTIFICATE OF CORRECTION

Patent No. 3,935,984      Dated February 3, 1976

Inventor(s) Abraham Lichowsky et al.

It is certified that error appears in the above-identified patent and that said Letters Patent are hereby corrected as shown below:

In the heading, the assignees should read:

-- [73] Assignee: Medical Monitors, Inc., Los Angeles, Calif. --

Signed and Sealed this first Day of June 1976

[SEAL]

Attest:

RUTH C. MASON
*Attesting Officer*

C. MARSHALL DANN
*Commissioner of Patents and Trademarks*